(12) United States Patent
Deno et al.

(10) Patent No.: US 11,291,398 B2
(45) Date of Patent: Apr. 5, 2022

(54) SYSTEM AND METHOD FOR SORTING ELECTROPHYSIOLOGICAL SIGNALS ON VIRTUAL CATHETERS

(71) Applicant: St. Jude Medical, Cardiology Division, Inc., St. Paul, MN (US)

(72) Inventors: Don Curtis Deno, Andover, MN (US); Eric S. Olson, St. Paul, MN (US); Dennis J. Morgan, Crystal, MN (US); Jeffrey A. Schweitzer, St. Paul, MN (US); Eric J. Voth, Maplewood, MN (US)

(73) Assignee: ST JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 238 days.

(21) Appl. No.: 16/242,420

(22) Filed: Jan. 8, 2019

(65) Prior Publication Data

US 2019/0209034 A1    Jul. 11, 2019

Related U.S. Application Data

(60) Provisional application No. 62/615,192, filed on Jan. 9, 2018.

(51) Int. Cl.
*A61B 5/04* (2006.01)
*A61B 5/339* (2021.01)
(Continued)

(52) U.S. Cl.
CPC ............... *A61B 5/339* (2021.01); *A61B 5/25* (2021.01); *A61B 5/341* (2021.01); *G16H 50/20* (2018.01); *A61B 5/389* (2021.01); *A61B 5/7246* (2013.01)

(58) Field of Classification Search
CPC . A61B 18/1492; A61B 5/042; A61B 5/04021; A61B 5/04023; A61B 5/0422;
(Continued)

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| EP | 3015060 A1 | 5/2016 | |
| WO | WO-0134026 A1 * | 5/2001 | ............... A61B 6/12 |

*Primary Examiner* — Michael J D'Abreu
(74) *Attorney, Agent, or Firm* — Wiley Rein, LLP (57) ABSTRACT

Electrophysiological signals from a graphical representation of an electrophysiology map including a plurality of electrophysiology data points can be sorted by receiving user inputs specifying a number of virtual electrodes for a virtual catheter and defining a pathway of the virtual catheter. A corresponding number of virtual electrodes can be defined on the pathway of the virtual catheter, and one or more electrophysiology data points relevant to electrical activity at the virtual electrodes can be identified, allowing output of a graphical representation of electrophysiological signals corresponding to the identified electrophysiology data points. Relevant electrophysiology data points can be identified by applying one or more relevance criterion, such as a distance criterion, a bipole orientation criterion, a time criterion, and/or a morphology criterion.

15 Claims, 5 Drawing Sheets

(51) Int. Cl.
*G16H 50/20* (2018.01)
*A61B 5/25* (2021.01)
*A61B 5/341* (2021.01)
*A61B 5/00* (2006.01)
*A61B 5/389* (2021.01)

(58) Field of Classification Search
CPC ................ A61B 5/0402; A61B 5/6852; A61B 2576/023
See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2011/0206256 A1 | 8/2011 | Ramanathan et al. |
| 2013/0072788 A1* | 3/2013 | Wu ........................ G06T 7/251 600/424 |
| 2015/0057507 A1 | 2/2015 | Koyrakh et al. |

* cited by examiner

FIG.5

SYSTEM AND METHOD FOR SORTING ELECTROPHYSIOLOGICAL SIGNALS ON VIRTUAL CATHETERS

CROSS-REFERENCE TO RELATED APPLICATIONS

This application claims the benefit of U.S. provisional application No. 62/615,192, filed 9 Jan. 2018, which is hereby incorporated by reference as though fully set forth herein.

BACKGROUND

The present disclosure relates generally to cardiac diagnostic and therapeutic procedures, such as electrophysiological mapping and cardiac ablation. In particular, the present disclosure relates to systems, apparatuses, and methods for sorting electrophysiological signals measured by multi-dimensional catheters, such as high density ("HD") grid catheters, on a virtual catheter.

High density electrophysiology maps can be constructed from thousands of electrophysiology data points. Extant electroanatomical mapping systems allow a practitioner to isolate a single electrophysiology data point within a map and review its associated electrophysiological signal. Extant systems do not, however, allow a practitioner to quickly and concurrently review the electrophysiological signals associated with neighboring points and/or the electrophysiological signals along a specified path, unless that path happens to coincide with that of an electrophysiology catheter used to collect the electrophysiology data points.

BRIEF SUMMARY

Disclosed herein is a method of sorting a plurality of electrophysiological signals from a graphical representation of an electrophysiology map generated by an electroanatomical mapping system, the electrophysiology map including a plurality of electrophysiology data points, the method including: receiving, via the electroanatomical mapping system, a user input specifying a number of virtual electrodes for a virtual catheter; receiving, via the electroanatomical mapping system, a user input defining a pathway of the virtual catheter; the electroanatomical mapping system defining a plurality of virtual electrodes on the pathway of the virtual catheter corresponding to the number of virtual electrodes; the electroanatomical mapping system identifying one or more electrophysiology data points of the plurality of electrophysiology data points relevant to electrical activity at the plurality of virtual electrodes; and the electroanatomical mapping system outputting a graphical representation of one or more electrophysiological signals corresponding to the identified one or more electrophysiology data points. In aspects of the disclosure, the user input defining a pathway of the virtual catheter can be a pathway traced by the user on the graphical representation of the electrophysiology map.

Various criteria can be applied in connection with the electroanatomical mapping system identifying one or more electrophysiology data points of the plurality of electrophysiology data points relevant to electrical activity at the plurality of virtual electrodes. For instance, the identifying step can include, for each virtual electrode of the plurality of virtual electrodes: the electroanatomical mapping system determining if one or more electrophysiology data points of the plurality of electrophysiology data points satisfies a distance criterion (e.g., a preselected maximum distance from the virtual electrode, such as between about 2 mm and about 6 mm); and if one or more electrophysiology data points satisfy the distance criterion, identifying the one or more electrophysiology data points as relevant to electrical activity at the virtual electrode.

In other embodiments of the disclosure, the identifying step can include, for each virtual electrode of the plurality of virtual electrodes: the electroanatomical mapping system identifying a closest electrophysiology data point to the virtual electrode of the identified one or more electrophysiology data points; and the electroanatomical mapping system associating the closest electrophysiology data point to the virtual electrode with the virtual electrode.

In still further embodiments of the disclosure, the identifying step can include, for each virtual electrode of the plurality of virtual electrodes: the electroanatomical mapping system applying one or more relevance criteria to the identified one or more electrophysiology data points, wherein the one or more relevance criteria include one or more of a bipole orientation criterion, a time criterion, and a morphology criterion; and the electroanatomical mapping system associating an electrophysiology data point of the identified one or more electrophysiology data points that satisfies the one or more relevance criteria with the virtual electrode. The bipole orientation criterion can include a preselected bipole orientation of the identified electrophysiology data point relative to a direction of the pathway of the virtual catheter. The time criterion can include a preselected collection time for the identified electrophysiology data point. The morphology criterion can include a correlation value, such as a Pearson correlation value, or a similarity metric for the identified electrophysiology data point relative to other electrophysiology data points of the plurality of electrophysiology data points relevant to electrical activity at the plurality of virtual electrodes.

It is contemplated that the order in which the electroanatomical mapping system outputs the graphical representation of the one or more electrophysiological signals corresponding to the identified one or more electrophysiology data points can correspond to a direction of the pathway of the virtual catheter. The electroanatomical mapping system can also output a graphical representation of the plurality of virtual electrodes on the graphical representation of the electrophysiology map and/or highlight the identified one or more electrophysiology data points on the graphical representation of the electrophysiology map.

Also disclosed herein is a method of sorting a plurality of electrophysiological signals from a graphical representation of an electrophysiology map generated by an electroanatomical mapping system, the electrophysiology map including a plurality of electrophysiology data points, the method including: receiving, via the electroanatomical mapping system, a user input defining a virtual catheter including a plurality of virtual electrodes; for each virtual electrode of the plurality of virtual electrodes, the electroanatomical mapping system applying one or more relevance criteria to the plurality of electrophysiology data points to identify no more than one electrophysiology data point that is relevant to electrical activity at the virtual electrode; and for each of the identified electrophysiology data points, the electroanatomical mapping system outputting a graphical representation of an electrophysiological signal associated with the identified electrophysiology data point. An order in which the electroanatomical mapping system outputs the graphical representations of the electrophysiological signals associated with the identified electrophysiology data points can correspond to a direction of the virtual catheter relative to the graphical representation of an electrophysiology map.

In aspects of the disclosure, the one or more relevance criteria includes a distance criterion, and can further include one or more of a bipole orientation criterion, a time criterion, and a morphology criterion.

The instant disclosure also provides a system for sorting a plurality of electrophysiological signals from a graphical representation of an electrophysiology map generated by an electroanatomical mapping system and including a plurality of electrophysiology data points. The system includes a sorting and visualization processor configured to: receive, via the electroanatomical mapping system, a user input specifying a number of virtual electrodes for a virtual catheter and a user input defining a pathway of the virtual catheter; define a virtual catheter extending along the pathway and including a plurality of virtual electrodes corresponding to the number of virtual electrodes; identify one or more electrophysiology data points of the plurality of electrophysiology data points relevant to electrical activity at the plurality of virtual electrodes; and output a graphical representation of one or more electrophysiological signals corresponding to the identified one or more electrophysiology data points. The sorting and visualization processor can be configured to identify the one or more electrophysiology data points relevant to electrical activity at the plurality of virtual electrodes by applying one or more relevance criteria, which can include one or more of a distance criterion, a bipole orientation criterion, a time criterion, and a morphology criterion, to the plurality of electrophysiology data points.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for sorting electrophysiological signals on a virtual catheter. For purposes of illustration, aspects of the disclosure will be described with reference to sorting cardiac electrophysiological signals (e.g., intracardiac electrograms measured using an HD grid catheter). It should be understood, however, that the teachings herein can be applied to good advantage in other contexts and/or with respect to other electrode configurations.

Figure 1:
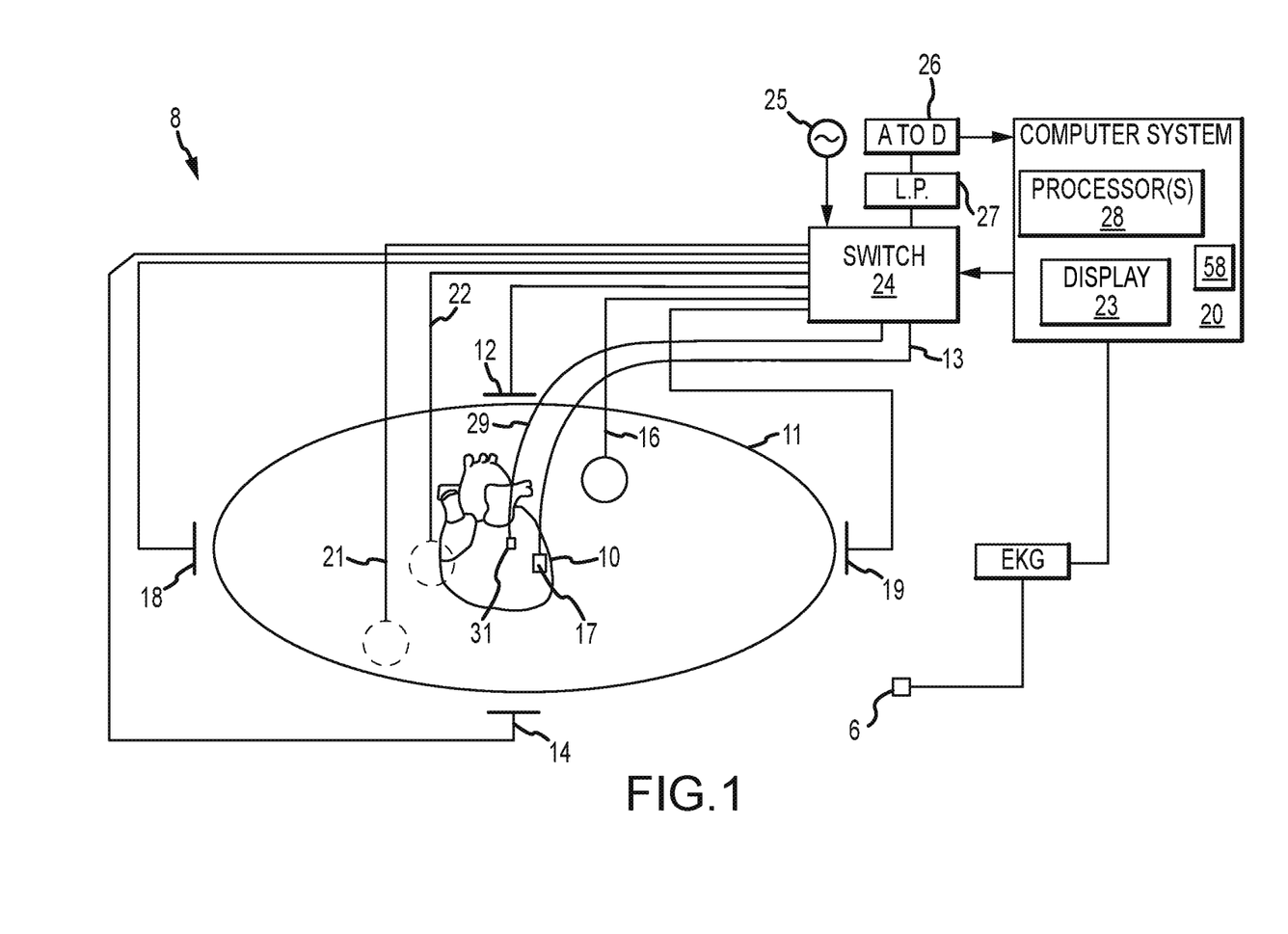
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create an electrophysiology map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
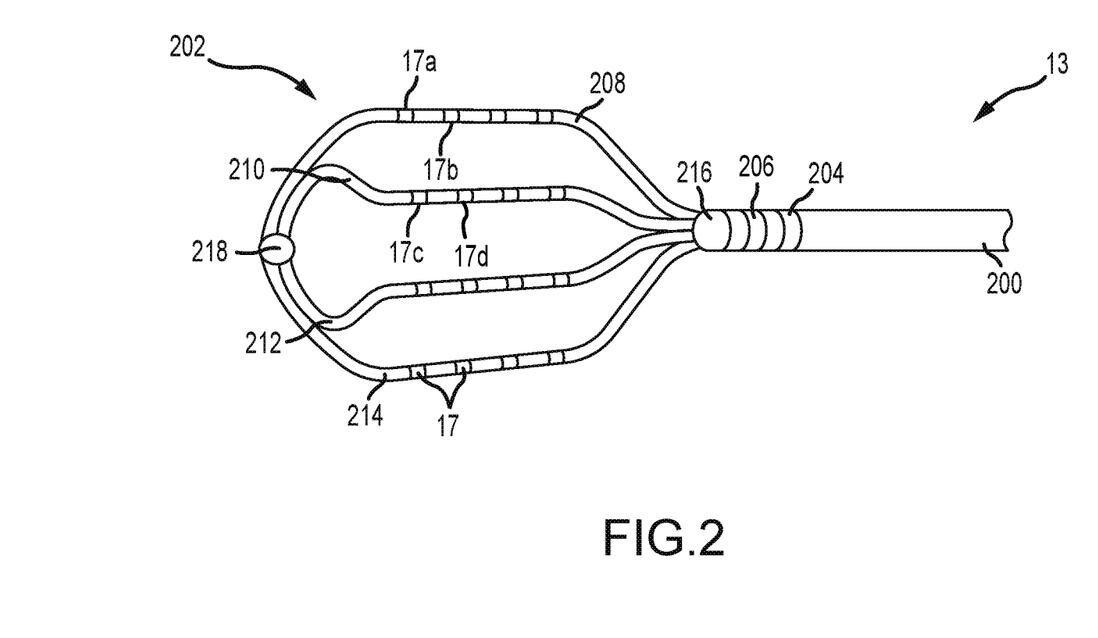
FIG. 2 depicts an exemplary catheter that can be used in connection with aspects of the instant disclosure.

In particular, for purposes of this disclosure, a segment of an exemplary multi-electrode catheter 13, often referred to as an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively).

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into the left ventricle of the patient's heart 10, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to the sorting of electrophysiological signals for a virtual catheter, for example in order to display graphical representations (e.g., traces) of the electrophysiological signals on display 23. System 8 can therefore also include a sorting and visualization module 58 that can be used to sort and generate graphical representations (e.g., traces) of electrophysiological signals on display 23. Those of ordinary skill in the art will be familiar with the graphical representation of electrophysiological signal traces in conjunction with electroanatomical mapping systems, such that a detailed description of the same is not necessary to an understanding of the instant disclosure.

Figure 3:
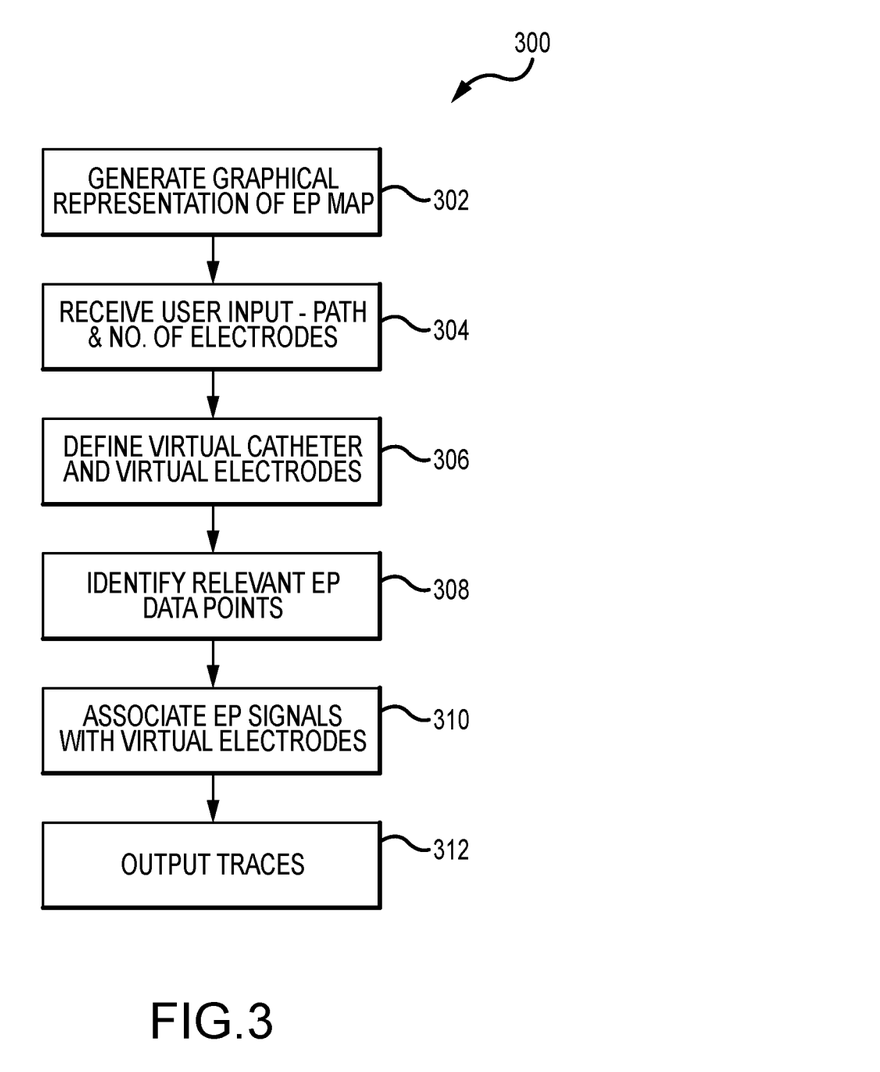
FIG. 3 is a flowchart of representative steps that can be followed according to exemplary embodiments disclosed herein.

One exemplary method of sorting and visualizing electrophysiological signals according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or sorting and visualization module 58). It should be understood that the representative steps described below can be either hardware- or software-implemented. For the sake of explanation, the term "signal processor" is used herein to describe both hardware- and software-based implementations of the teachings herein.

Figure 4:
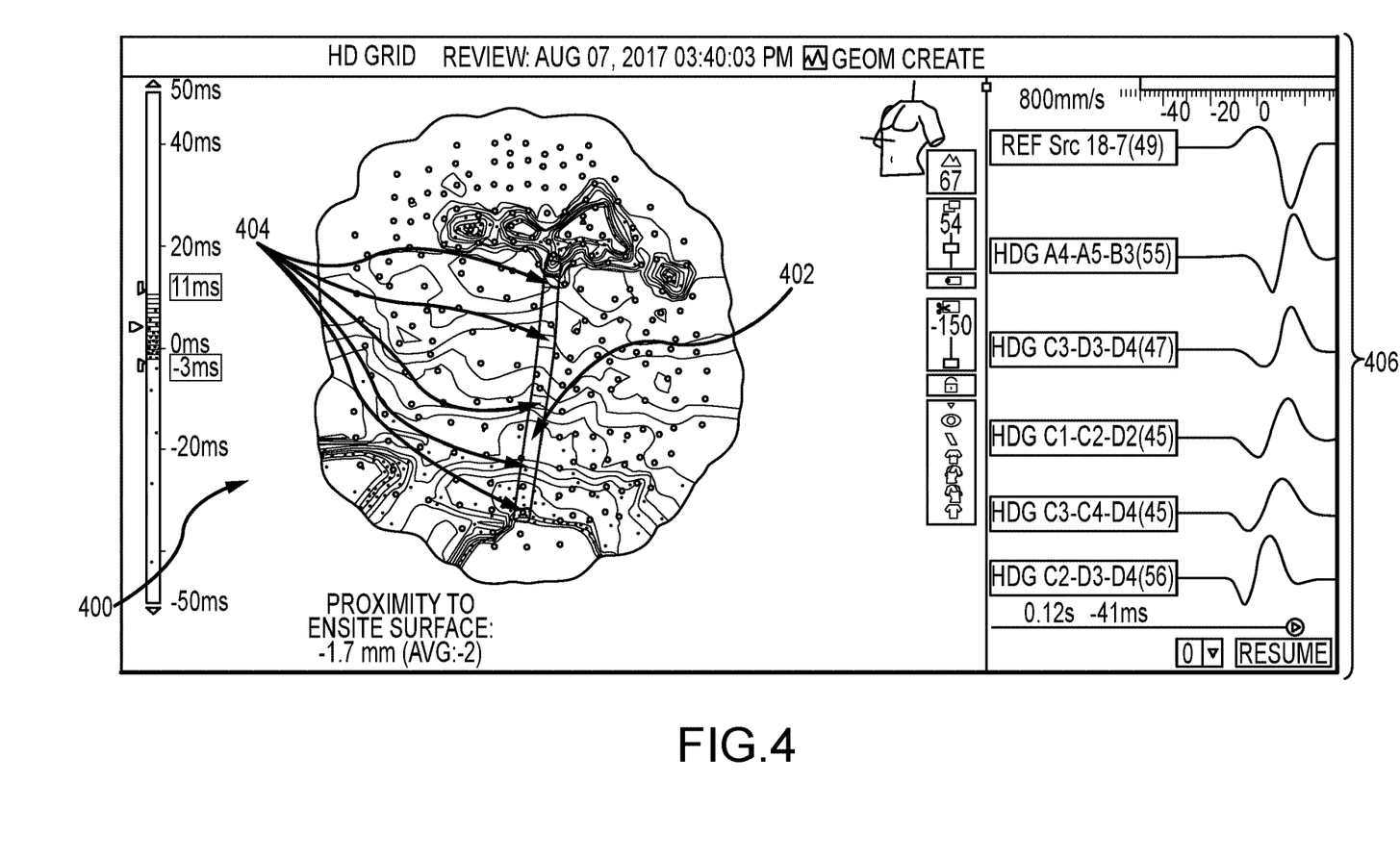
FIG. 4 illustrates an electrophysiology map and a virtual catheter.

In block 302, system 8 generates a graphical representation of an electrophysiology map, such as a map of local activation time, voltage, fractionation, conduction velocity, or the like, and including a plurality of electrophysiology data points. As discussed above, those of ordinary skill in the art will be familiar with the graphical representation of electrophysiology maps by electroanatomical mapping systems, such that a detailed discussion of the same is not necessary herein. For purposes of illustration, however, FIG. 4 depicts a representative electrophysiology map in the form of local activation time map 400. Those of ordinary skill in the art will also recognize that each electrophysiology data point includes both location data and electrophysiology data (e.g., an intracardiac electrogram and a position on the heart where the intracardiac electrogram was measured).

In block 304, system 8 receives user input, such as through a graphical user interface ("GUI"), to define a virtual electrophysiology catheter. For example, the user can define a pathway of the virtual catheter, relative to electrophysiology map 400, such as by tracing a pathway 402 on electrophysiology map 400. The user can also specify a number of virtual electrodes 404 for the virtual catheter.

In block 306, system 8 defines the virtual catheter, including the desired number of virtual electrodes 404 thereon, according to the user input from block 304. For instance, FIG. 4 depicts five virtual electrodes 404, which are evenly spaced along pathway 402 that defines the virtual catheter. FIG. 4 also depicts electrograms 406 corresponding to virtual electrodes 404, which can be generated from relevant electrophysiology data points according to the teachings below.

In block 308, system 8 identifies one or more electrophysiology data points of the plurality of electrophysiology data points that make up electrophysiology map 400 that are relevant to electrical activity at the virtual electrodes defined in block 306. For purposes of the instant disclosure, an electrophysiology data point is relevant to electrical activity at a virtual electrode if it satisfies one or more relevance criteria vis-à-vis the virtual electrode.

Many electrophysiology data points may therefore be relevant to electrical activity at a virtual electrode. It should be understood, however, that, in aspects of the disclosure, only one such relevant electrophysiology data point (more particularly, the electrophysiological signal thereof) will ultimately be associated with the virtual electrode. In other embodiments of the disclosure, a composite of the electrophysiological signals from multiple such relevant electrophysiology data points can be associated with the virtual electrode. In still other aspects of the disclosure, the number of virtual electrodes can be increased, which correspondingly increases the number of relevant electrophysiology data points. Of course, it is also contemplated that there may be no electrophysiology data points relevant to electrical activity at a particular virtual electrode (that is, there may be no electrophysiology data points that satisfy the one or more relevance criteria vis-à-vis the virtual electrode), in which case no electrophysiology data point, and thus no electrophysiological signal, will be associated with that virtual electrode.

A first order relevance criterion is a distance criterion, which can be implemented as a maximum distance (e.g., Euclidean distance, geodesic distance) from the location of the virtual electrode. The maximum distance can be user defined or a system preset, and will typically be between about 2 mm and about 6 mm. Any electrophysiology data points falling within the maximum distance from the location of the virtual electrode (e.g., any electrophysiology points falling within a sphere centered at the virtual electrode and having a radius of the maximum distance) can be deemed to satisfy the distance criterion.

In some embodiments of the disclosure, only a distance criterion is applied. In such instances, if more than one electrophysiology data point satisfies the distance criterion, the electrophysiology point that is closest to the location of the virtual electrode can have its associated electrophysiological signal associated with the virtual electrode.

Figure 5:
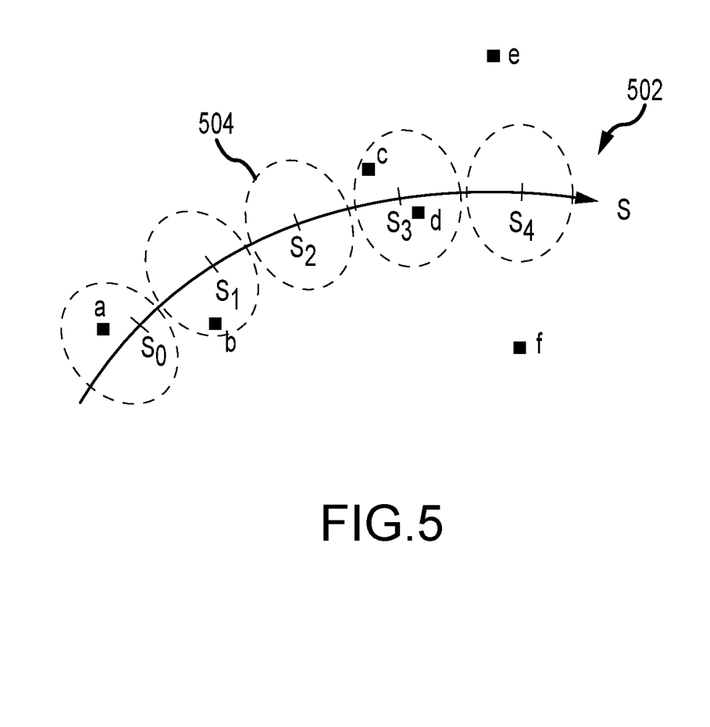
FIG. 5 illustrates the use of a distance criterion to identify electrophysiology data points relevant to electrical activity at several virtual electrodes.

For example, FIG. 5 schematically depicts a virtual catheter 502 having a plurality of virtual electrodes $s_0$, $s_1$, $s_2$, etc. FIG. 5 also depicts a plurality of electrophysiology data points a, b, c, d, e, and f. About each virtual electrode is a dashed circle 504 representing the distance criterion. As shown in FIG. 5, electrophysiology data point a falls within the dashed circle 504 surrounding virtual electrode $s_0$, electrophysiology data point b falls within the dashed circle 504 surrounding virtual electrode $s_1$, electrophysiology data points c and d fall within the dashed circle 504 surrounding virtual electrode $s_3$, and no electrophysiology data points fall within the dashed circles 504 surrounding virtual electrodes $s_2$ and $s_4$.

Thus, the electrophysiological signal of electrophysiology data point a can be associated with virtual electrode $s_0$ and the electrophysiological signal of electrophysiology data point b can be associated with virtual electrode $s_1$. Because electrophysiology data point d is closer to virtual electrode $s_3$ than electrophysiology data point c, the electrophysiological signal of electrophysiology data point c can be associated with virtual electrode $s_3$. No electrophysiological signal will be associated with virtual electrodes $s_2$ and $s_4$.

A distance criterion can also treat distance from virtual catheter 502 differently from distance along virtual catheter 502. For instance, instead of using a distance criterion that can be represented by a spherical (or, as shown in two dimensions in FIG. 5, circular) construct, a distance criterion can be represented by a cylindrical construct, which can be centered on the virtual electrode (e.g., $s_0$, $s_1$, $s_2$, etc.) and can have a height along the length of virtual catheter 502.

Additional relevance criterion include, without limitation, bipole orientation criteria, collection time criteria, and morphology criteria. Each of these will be discussed in turn below.

A bipole orientation criterion can be used when the electrophysiological signals associated with the electrophysiology data points making up electrophysiology map 400 are bipolar electrograms. A bipole orientation criterion evaluates the orientation of the bipole of the electrophysiology data point relative to a reference orientation. For example, the bipole orientation criterion can be defined to evaluate whether the bipole of the electrophysiology data point is along the direction of pathway 402 of the virtual catheter. Alternatively, the bipole orientation criterion can be defined to evaluate whether the bipole of the electrophysiology data point is perpendicular to the direction of pathway 402 of the virtual catheter. Desirably, the use of a bipole orientation criterion increases the likelihood that the electrophysiological signals ultimately associated with each of the virtual electrodes will have the same or similar bipole orientations. In aspects of the disclosure, the bipole orientation criterion is a range of between about 36 degrees and about 40 degrees, centered on the direction of pathway 402 of the virtual catheter.

A collection time criterion helps ensure that the electrophysiological signals ultimately associated with each of the virtual electrodes was collected at approximately the same time. The collection time criterion can be an absolute criterion, measured from a single time datum (e.g., measured from the start of the electrophysiology study) or a relative criterion, measured from a recurring datum (e.g., measured from the start of depolarization on any given beat). In other embodiments of the disclosure, the datum can be an average (e.g., mean or median) collection time of electrophysiology data points proximate a virtual electrode (e.g., that satisfy a distance criterion, as discussed above).

A morphology criterion helps ensure that the electrophysiological signals ultimately associated with each of the virtual electrodes have similar morphologies (similar to each other and/or to a template morphology). A morphology criterion can be expressed as a minimum morphology matching score, which can be computed, for example, using a correlation value or similarity metric; one exemplary correlation value is the Pearson Correlation Coefficient. Additional detail regarding morphology matching scores can be found in United States application publication no. 2015/0057507, which is hereby incorporated by reference as though fully set forth herein.

In block 310, no more than one electrophysiological signal is associated with each virtual electrode. As discussed above, it is contemplated that, if no electrophysiology data point satisfies the relevance criteria vis-à-vis a particular virtual electrode, no electrophysiological signal may be associated with that virtual electrode.

Figure 6:
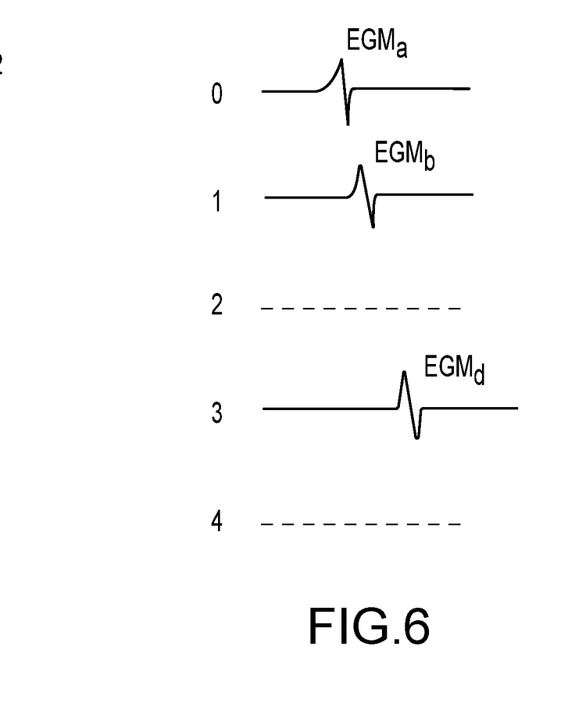
FIG. 6 is a representation of electrophysiological activity at a plurality of virtual electrodes according to aspects of the teachings herein.

In block 312, system 8 outputs a graphical representation of the electrophysiological signals associated with the virtual electrodes, for example as a plurality of traces on display 23 according to techniques that will be familiar to the ordinarily skilled artisan. The order in which the traces are output can correspond to a direction of the pathway of virtual catheter 402 on electrophysiology map 400. For example, FIG. 6 depicts a representative output of a plurality of traces corresponding to the schematic virtual catheter 502 of FIG. 5.

Although several embodiments have been described above with a certain degree of particularity, those skilled in the art could make numerous alterations to the disclosed embodiments without departing from the spirit or scope of this invention.

For example, system 8 can display graphical representations of the virtual electrodes on the graphical representation of the electrophysiology map. As another example, the electrophysiology data points identified as relevant to the electrical activity at the virtual electrodes can be highlighted on the graphical representation of the electrophysiology map.

As another example, in addition to being used as part of a bipole orientation criterion, the direction of pathway 402 of the virtual catheter can also be used to specify the direction along which a 2D electrogram signal (e.g., as part of an omnipolar voltage loop) can be projected.

As yet a further example, instead of defining a virtual catheter including a plurality of virtual electrodes, all electrophysiology data points within a preset distance of the defined pathway (e.g., pathway 402) can be used.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of sorting a plurality of electrophysiological signals from a graphical representation of an electrophysiology map generated by an electroanatomical mapping system, the electrophysiology map comprising a plurality of electrophysiology data points, the method comprising:
receiving, via the electroanatomical mapping system, a user input specifying a number of virtual electrodes for a virtual catheter;
receiving, via the electroanatomical mapping system, a user input defining a pathway of the virtual catheter;
the electroanatomical mapping system defining the virtual catheter corresponding to the pathway specified by the user and a plurality of virtual electrodes on the virtual catheter corresponding to the number of virtual electrodes specified by the user;
the electroanatomical mapping system identifying one or more electrophysiology data points of the plurality of electrophysiology data points relevant to electrical activity at the plurality of virtual electrodes;
the electroanatomical mapping system outputting a graphical representation of one or more electrophysiological signals corresponding to the identified one or more electrophysiology data points; and
the electroanatomical mapping system outputting a graphical representation of the virtual catheter, including the plurality of virtual electrodes thereon, on the graphical representation of the electrophysiology map.

2. The method according to claim 1, wherein the electroanatomical mapping system identifying one or more electrophysiology data points of the plurality of electrophysiology data points relevant to electrical activity at the plurality of virtual electrodes comprises, for each virtual electrode of the plurality of virtual electrodes:
the electroanatomical mapping system determining if one or more electrophysiology data points of the plurality of electrophysiology data points satisfies a distance criterion; and
if one or more electrophysiology data points satisfy the distance criterion, identifying the one or more electrophysiology data points as relevant to electrical activity at the virtual electrode.

3. The method according to claim 2, wherein the electroanatomical mapping system identifying one or more electrophysiology data points of the plurality of electrophysiology data points relevant to electrical activity at the plurality of virtual electrodes further comprises, for each virtual electrode of the plurality of virtual electrodes:
the electroanatomical mapping system applying one or more relevance criteria to the identified one or more electrophysiology data points, wherein the one or more relevance criteria comprise one or more of a bipole orientation criterion, a time criterion, and a morphology criterion; and
the electroanatomical mapping system associating an electrophysiology data point of the identified one or more electrophysiology data points that satisfies the one or more relevance criteria with the virtual electrode.

4. The method according to claim 3, wherein the bipole orientation criterion comprises a preselected bipole orientation of the identified electrophysiology data point relative to a direction of the pathway of the virtual catheter.

5. The method according to claim 3, wherein the time criterion comprises a preselected collection time for the identified electrophysiology data point.

6. The method according to claim 3, wherein the morphology criterion comprises at least one of a correlation value or a similarity metric for the identified electrophysiology data point relative to other electrophysiology data points of the plurality of electrophysiology data points relevant to electrical activity at the plurality of virtual electrodes.

7. The method according to claim 2, wherein the distance criterion comprises a preselected maximum distance from the virtual electrode.

8. The method according to claim 7, wherein the maximum distance is between 2 mm and 6 mm.

9. The method according to claim 2, wherein the electroanatomical mapping system identifying one or more electrophysiology data points of the plurality of electrophysiology data points relevant to electrical activity at the plurality of virtual electrodes further comprises, for each virtual electrode of the plurality of virtual electrodes:
the electroanatomical mapping system identifying a closest electrophysiology data point to the virtual electrode of the identified one or more electrophysiology data points; and
the electroanatomical mapping system associating the closest electrophysiology data point to the virtual electrode with the virtual electrode.

10. The method according to claim 1, wherein the user input defining a pathway of the virtual catheter comprises a pathway traced by the user on the graphical representation of the electrophysiology map.

11. The method according to claim 1, wherein an order in which the electroanatomical mapping system outputs the graphical representation of the one or more electrophysiological signals corresponding to the identified one or more electrophysiology data points corresponds to a direction of the pathway of the virtual catheter.

12. The method according to claim 1, further comprising the electroanatomical mapping system highlighting the identified one or more electrophysiology data points on the graphical representation of the electrophysiology map.

13. A system for sorting a plurality of electrophysiological signals from a graphical representation of an electrophysiology map generated by an electroanatomical mapping system and including a plurality of electrophysiology data points, the system comprising:
a sorting and visualization processor configured to:
receive, via the electroanatomical mapping system, a user input specifying a number of virtual electrodes for a virtual catheter and a user input defining a pathway of the virtual catheter;
define a virtual catheter extending along the pathway and including a plurality of virtual electrodes corresponding to the number of virtual electrodes;
identify one or more electrophysiology data points of the plurality of electrophysiology data points relevant to electrical activity at the plurality of virtual electrodes;
output a graphical representation of one or more electrophysiological signals corresponding to the identified one or more electrophysiology data points; and
output a graphical representation of the virtual catheter, including the plurality of virtual electrodes, on the graphical representation of the electrophysiology map.

14. The system according to claim 13, wherein the sorting and visualization processor is configured to identify the one or more electrophysiology data points relevant to electrical activity at the plurality of virtual electrodes by applying one or more relevance criteria to the plurality of electrophysiology data points.

15. The system according to claim 14, wherein the one or more relevance criteria comprise one or more of a distance criterion, a bipole orientation criterion, a time criterion, and a morphology criterion.

* * * * *